United States Patent
Krüger (10) Patent No.: US 10,335,561 B2
(45) Date of Patent: Jul. 2, 2019

(54) VALVE (71) Applicant: PARI GmbH Spezialisten für effektive Inhalation, Starnberg (DE)

(72) Inventor: Ulf Krüger, Munich (DE)

(73) Assignee: PARI GmbH Spezialisten für effektive Inhalation, Starnberg (DE)

( * ) Notice: Subject to any disclaimer, the term of this patent is extended or adjusted under 35 U.S.C. 154(b) by 0 days.

(21) Appl. No.: 15/444,395

(22) Filed: Feb. 28, 2017

(65) Prior Publication Data
US 2017/0252524 A1  Sep. 7, 2017

(30) Foreign Application Priority Data

Mar. 2, 2016  (EP) .................................. 16158227

(51) Int. Cl.
| *F16K 15/14* | (2006.01) |
| *A61M 15/00* | (2006.01) |
| *A61M 16/20* | (2006.01) |
| *A61M 39/24* | (2006.01) |

(52) U.S. Cl.
CPC ...... *A61M 15/0013* (2014.02); *A61M 15/009* (2013.01); *A61M 16/208* (2013.01); *F16K 15/147* (2013.01); *A61M 2039/2426* (2013.01)

(58) Field of Classification Search
CPC .......... A61M 2039/2426; A61M 39/24; A61M 15/0013; F16K 15/147
USPC ....................................... 137/846
See application file for complete search history.

(56) References Cited

U.S. PATENT DOCUMENTS

| 3,504,699 | A | * | 4/1970 | Grise ................... F16K 15/147 137/846 |
| 4,148,420 | A | * | 4/1979 | Morrissette ........ B65D 47/2031 137/846 |
| 6,585,005 | B1 | * | 7/2003 | Raftis ................... F16K 15/147 137/846 |
| 7,445,028 | B1 | | 11/2008 | Aanonsen et al. |
| 2004/0069360 | A1 | | 4/2004 | Raftis |
| 2005/0187524 | A1 | | 8/2005 | Willis et al. |
| 2011/0108139 | A1 | | 5/2011 | Wright et al. |

FOREIGN PATENT DOCUMENTS

| EP | 1 077 339 A2 | 2/2001 |
| EP | 2 008 678 A2 | 12/2008 |

OTHER PUBLICATIONS

European Examination Report and English language machine translation thereof dated Aug. 17, 2016 in connection with European Application No. 16158227.5.

* cited by examiner

Primary Examiner — P. Macade Nichols
(74) Attorney, Agent, or Firm — Wolf, Greenfield & Sacks, P.C.

(57) ABSTRACT

A valve (1, 11, 19) for an inhalation device comprising an interior volume that is delimited at least partially by a valve wall (4, 17, 21), a permanent opening (29) as well as a valve functional area (6), whereby the valve functional area (6) is configured to be at least almost closed below an opening pressure difference and to be open above an opening pressure difference such that above the opening pressure difference, a fluid can flow through the permanent opening (29) into the interior volume and out of the valve functional area (6), the valve comprising an inversion protector that is configured to impede or prevent inversion of the valve wall (4, 17, 21).

5 Claims, 6 Drawing Sheets

VALVE

The invention relates to a valve for an inhalation device.

Valves for inhalation devices are known from the prior art and are described, for example, in EP 2 008 678 A2. EP 2 008 678 A2 describes a one-piece two-way valve system that allows inhalation and exhalation with a single valve. The valve has a base, a first valve element, which has a duck-bill shape in one embodiment, and a second valve element, which is shaped like a hinged flap in one embodiment.

When in operation, valves for inhalation devices should, from any state, be able to assume an open state and a closed state or an at least almost closed state. For this purpose, possible deformations of the valve should be restricted. This leads to restrictions in the selection of suitable geometries and materials for the valve. The object of the invention is therefore to provide a valve having a reliable valve function and for which there is nevertheless a high degree of freedom of design with regard to the geometries and materials used.

This object is solved by a valve for an inhalation device comprising an interior volume that is delimited at least partially by a valve wall, a permanent opening as well as a valve functional area, the valve functional area being configured to be at least almost closed below an opening pressure difference and to be open above an opening pressure difference such that above the opening pressure difference, a fluid can flow through the permanent opening into the interior volume and out of the valve functional area, the valve comprising an inversion protector that is configured to impede or prevent inversion of the valve wall.

The valve expediently comprises a flow-throughable interior volume. It is preferably a duckbill valve, a cross-slit valve or a joker valve.

The duckbill valve is preferably a one-piece cast valve. The duckbill valve is preferably configured to reliably prevent a backflow at low pressure differences. Below an opening pressure difference, a duckbill valve expediently comprises a slit as the valve functional area, which is configured to form an opening above an opening pressure difference. A slit is expediently an elongated gap. The slit is preferably delimited by two areas of the valve wall that come together without overlapping in the at least almost closed state. The slit can be provided between two areas of the valve wall which lie against one another or close to one another in the at least almost closed state. In a preferred embodiment, two areas of the valve wall lie against one another via their inner sides in the closed state. The valve functional area is expediently configured to form an opening in that the areas of the valve wall move away from one another.

Below an opening pressure difference, a cross-slit valve comprises two slits as the valve functional area, which together form a cross shape and are also configured to form an opening above an opening pressure difference.

Below an opening pressure difference, three slits are provided in a joker valve as the valve functional area, which meet at a point in such a manner that three slits extend radially outwards from this point. These slits are also configured to form an opening above the opening pressure difference.

The slits of the cross-slit valve and the joker valve are also preferably delimited by two areas of the valve wall which meet one another obtusely in the at least almost closed state. The slits can be provided between areas of the valve wall which lie against one another or close to one another in the at least almost closed state. In a preferred embodiment, areas of the valve walls lie against one another via their inner sides in the closed state. The valve functional area is expediently configured to form an opening in that the areas of the valve walls move away from one another.

The inhalation device preferably comprises an aerosol generating device. An aerosol generating device preferably comprises a nebulizer, an atomizer, a humidifier, a compressed air nebulizer, an air atomizer, an electronic nebulizer, an ultrasonic nebulizer, an electrohydrodynamic nebulizer, an electrostatic nebulizer, a membrane nebulizer, a nebulizer having a vibrating membrane, an electronic nebulizer having a vibrating membrane, a mesh nebulizer, a nozzle nebulizer, a metered dose inhaler (MDI), a powder inhaler (DPI) or a combination thereof. In one embodiment, the metered dose inhaler comprises a pressurized canister comprising a medicament and a propellant. The canister is expediently connected to an actuator that can be operated by hand. It is advantageous for the metered dose inhaler to be configured so as to release a specific amount of medicament in aerosol form upon activation. In one embodiment, the aerosol generating device is configured for use with ventilators.

It is advantageous for the inhalation device to comprise a device for providing aerosols. The device for providing aerosols preferably comprises an inhalation aid, a spacer or a chamber. Devices for providing aerosols are preferably devices that are intended for use with metered dose inhalers (MDIs). They provide a storage space that is suitable for accommodating aerosol preferably from metered dose inhalers such that it can be inhaled therefrom by users. Spacers do not comprise inhalation and exhalation valves, and a user should thus coordinate their breathing such that they do not exhale into the spacer. Chambers or holding chambers comprise exhalation and preferably also inhalation valves. It can thus be achieved that an exhaled air flow is not guided into the space in which the aerosol is located. It can be achieved that a medicament can only exit the storage space upon inhalation. The device for providing aerosols can comprise a storage space for accommodating and providing an aerosol, a nozzle for generating the aerosol, and a holder for a medicament canister. The medicament canister is thereby provided to supply a medicament for aerosol generation.

Aerosols are mixtures of solid or liquid suspended particles and a gas.

Aerosols are preferably provided for application on or in parts of the human or animal body such as the skin, body cavities, body orifices, the nose, the paranasal sinuses, the maxillary sinus, the frontal sinus, the sphenoidal sinus, the ethmoidal cells, the throat, the larynx, the trachea, the lungs, the stem bronchus, the bronchi, the bronchioles, the pulmonary alveoli, the joints or the abdominal cavity. Aerosols can be used to diagnose, prevent or treat diseases in humans and animals or to immunize humans or animals against diseases.

An interior volume is a volume that is at least partially surrounded by one or more components. The interior volume can have one opening or a plurality of openings to its surroundings. The interior volume can be delimited by a valve functional area that can assume an open and a closed state.

A valve wall preferably comprises a plastic, particularly preferred an elastomer, a silicone or a rubber. The valve wall expediently delimits a volume from its surroundings. The valve wall preferably delimits a flow-throughable volume.

A permanent opening of a valve is an opening that is always open when the valve is in operation. It is advantageous for the permanent opening to always have the same size when the valve is in operation.

A valve functional area is an area of a valve that can be both at least almost closed as well as open. The valve functional area is expediently configured to be at least almost closed or to be open depending on the existing pressure difference between the surroundings and an interior volume. It is advantageous for the valve functional area to be open above an opening pressure difference and to be closed below the opening pressure difference.

The opening pressure difference is a predetermined pressure difference, above which a valve functional area should be open and below which the valve functional area should be closed.

A fluid preferably contains a gas, a liquid or an aerosol.

Inversion is a turning in such a manner that thereafter the outer side is on the inside and the inner side is on the outside. In the case of a valve, inversion can occur in such a manner that starting from a valve functional area, a valve wall rolls up, the valve functional area passes through the permanent opening, and the valve wall unrolls again. In this state, the valve can no longer open and close as intended.

An inversion protector is a device that is suitable for impeding, limiting or preventing inversion of the valve.

The inversion protector preferably comprises a reinforcing region of the valve wall. The inversion protector can thereby be provided in a particularly simple manner.

In one embodiment, a foreign material was integrated into the valve as a reinforcing region using a two-component process. A hard component was preferably injected or sprayed into the valve.

The reinforcing region of the valve can be provided on an inner side or an outer side of the valve.

The reinforcing region expediently comprises a stiffener. The stiffener can be provided on the flat or planar side of a duckbill valve. Stiffeners can be provided in the interior of the valve or from the outside.

In one embodiment, cylindrical side parts of a duckbill valve are provided with a reinforcing region.

A particularly strong stiffening can be achieved by the combination of stiffeners on cylindrical side parts and on flat sides of a duckbill valve.

The reinforcing region of the valve wall is preferably an elongated region, the length of which is greater than the width. The reinforcing region thereby extends from the valve functional area or from the vicinity of the valve functional area in the direction of the permanent opening.

The reinforcing region is preferably configured as a thickened region. The thickness of the thickened region preferably corresponds to between double to twenty times the thickness of the valve wall, particularly preferred two to six times the thickness of the valve wall.

The thickened region is preferably provided on an inner side of the valve wall. In one embodiment, the thickened region is provided on an outer side of the valve wall. It can be advantageous to provide the thickened region both on an inner side and on an outer side of the valve wall.

In one embodiment, the reinforcing region is configured such that the valve is laterally stiffened. The valve is preferably stiffened by means of profiles. It is particularly preferred for the profiles to be built directly into the material. The bending stiffness can thereby be increased particularly well.

If the reinforcing region of the valve wall is at a distance to the permanent opening, it can be achieved in a particularly simple manner that the opening and closing of the valve occurs such that it is only impeded to a limited extent or is not impeded at all by the reinforcing region of the valve wall. The valve is expediently configured such that upon opening and closing, it deforms primarily in the region directly at the permanent opening. The region directly at the permanent opening preferably acts as a flexible joint.

It is advantageous for the reinforcing region to be provided on the valve wall in such a manner that the point of rotation of the side walls remains identical for opening of the valve. The lower region of the valve is expediently kept free to define the point of rotation. It can thereby be achieved that the joint is free, the valve opens easily and the force required to open the valve does not increase.

The distance of the reinforcing region of the valve wall from the permanent opening preferably corresponds to at least the thickness of the valve wall. The distance of the reinforcing region of the valve wall from the permanent opening is thereby expediently at most so large that there is just still space for the reinforcing region. It is particularly preferred for the distance of the reinforcing region of the valve wall from the permanent opening to be one to five times the thickness of the valve wall.

In one embodiment, the valve wall comprises a functional material and the reinforcing region of the valve wall comprises a support material. The support material thereby has a higher modulus of elasticity than the functional material. In this manner, a high supporting effect can be achieved with a comparatively low material volume. It is possible to provide good support the valve wall with a relatively thin design.

The valve can be completely or partially produced using the multicomponent injection molding process, preferably using the two-component injection molding process.

The reinforcing region of the valve wall having the support material preferably has the same thickness as the surrounding valve wall. Dirt-collecting edges can therefore be avoided in a simple manner. If the support material is provided on an outer side of the valve wall, the support material can be applied to the valve wall in a particularly simple manner. By arranging the support material on an inner side of the valve wall, a particularly effective supporting effect can be achieved.

A functional material preferably has a modulus of elasticity of between 0.003 and 5 $kN/mm^2$, particularly preferred between 0.01 and 0.1 $kN/mm^2$. A support material preferably has a modulus of elasticity of between 1 and 500 $kN/mm^2$, particularly preferred between 1 and 50 $kN/mm^2$.

The functional material preferably comprises an elastomer, particularly preferred a thermoplastic elastomer, silicone or rubber. The support material preferably comprises a polymer, particularly preferred polypropylene, polyethylene, polycarbonate, polystyrene, polyamide, polyoxymethylene, a thermoplastic, a reinforced thermoplastic, a fiber-reinforced thermoplastic, natural fibers or glass fibers.

If the reinforcing region of the valve wall abuts the valve functional area, rolling up of the valve wall starting from the valve functional area can be stopped from the outset in a particularly simple manner. In a preferred embodiment, the reinforcing region extends up to a slit of the valve functional area.

In one embodiment, the valve functional area is configured to have a slit below an opening pressure difference and the reinforcing region of the valve wall is configured to abut an end of the slit below an opening pressure difference. Tearing of the slit can be prevented or made more difficult in this manner.

In one embodiment, the reinforcing region preferably extends from the end of the slit or from the vicinity of the end of the slit along the shortest path or almost along the shortest path in the direction of the permanent opening. This embodiment is particularly expedient in connection with a duckbill valve. In some embodiments of the valve, the region between the end of the slit and the permanent opening is a region that only deforms to a limited extent or does not deform at all upon opening and closing of the valve functional area. By providing the reinforcing region in this region, opening and closing is therefore only impeded to a limited extent or is not impeded at all.

It is advantageous for the valve functional area to be configured to have a slit below an opening pressure difference and for the reinforcing region of the valve wall to abut the center of the slit below an opening pressure difference. The reinforcing region preferably extends in the direction of the permanent opening. In particular in the case of a duckbill valve, the reinforcing region preferably extends from a center of the slit of the duckbill valve along the shortest path in the direction of the permanent opening.

It is thereby possible in a simple manner to provide the reinforcing region at a position of the valve wall that is only deformed to a limited extent or is not deformed at all upon opening and closing of the valve functional area. The reinforcing region thereby does not impede opening and closing of the valve functional area at all or only does so to a very limited extent. The valve can therefore be designed more simply such that it already opens at slight pressure differences or at negative pressures.

In one embodiment, the inversion protector comprises a support member or a valve geometry for a valve wall. The support member advantageously comprises an abutment area for a valve wall. The abutment area is expediently configured such that a region of the valve wall can abut thereagainst. In such a manner, movement of the valve wall can be limited in a particularly simple way. It is particularly advantageous for the abutment area to be an abutment surface or an abutment edge. Inversion can thus be prevented in a particularly simple manner without impeding opening and closing. The support member is preferably connected to a valve carrier, which is configured to hold the valve. The support member is preferably integrated in the valve carrier.

The support member preferably comprises a support material, expediently a hard component. The support member is expediently arranged on an inner side of a valve wall. The support member is preferably arranged such that upon opening of the valve functional area, a valve wall comes into abutment with the support member when the opening has assumed a pass-through state, in which a provided passage is formed. No further movement of the valve functional area in the direction of the permanent opening is preferably possible when the valve wall abuts the support member.

In one embodiment, the support member is directed towards the flat side of a duckbill valve. The support member can have a continuous strut. In one embodiment, the support member has the shape of an antenna.

The support member is expediently configured to abut an inner side of the valve wall below an opening pressure difference. Inversion can hereby be limited or prevented in a particularly precise manner. Since the support member abuts the inner side of the valve wall, the valve wall does not have to first of all deform until it abuts the support member, and the inversion process can be limited or stopped. It is therefore easily possible to stop the inversion process in an early phase.

It is advantageous for the inversion protector to have a passage dividing device, which is configured to divide a flow of fluid through the interior volume into at least two smaller flows of fluid. Larger foreign bodies can be filtered out. Larger foreign bodies can thus be prevented from passing through the valve. The passage dividing device expediently comprises a bar. In one embodiment, the passage dividing device comprises a perforated plate or a net.

The invention will be described in more detail in the following by means of embodiments and making reference to the enclosed drawings.

Figure 1:
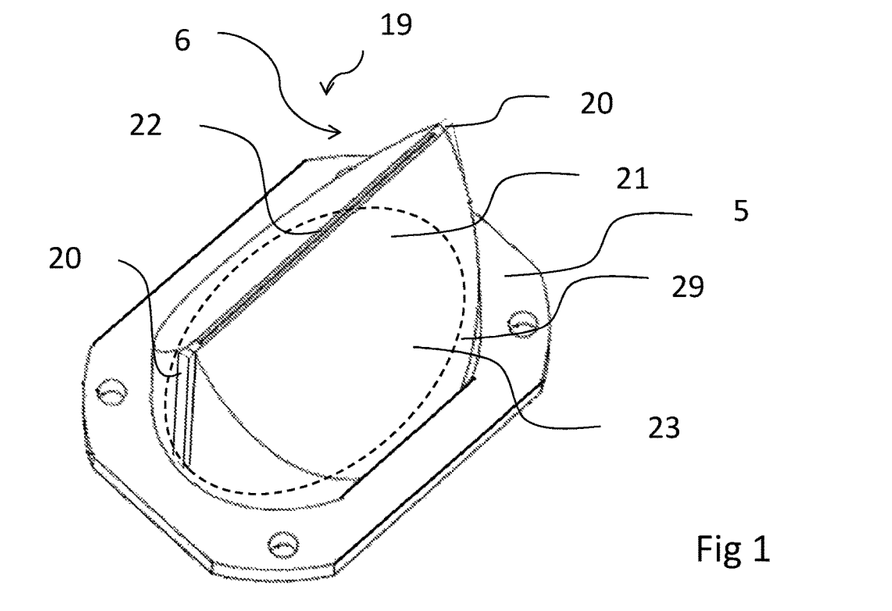
FIG. 1 shows a duckbill valve with two duckbill reinforcements.

FIG. 1 shows a duckbill valve 19 having two duckbill reinforcements 20. The duckbill valve 19 comprises a duckbill valve wall 21, which extends from a valve base 5 to a valve functional area 6. The duckbill valve wall 21 is made from a thermoplastic elastomer. A permanent opening 29 is provided in the valve base 5. The valve functional area 6 comprises a duckbill valve slit 22. When the pressure in the interior volume exceeds the surrounding pressure such that an opening pressure difference exists, the duckbill valve slit 22 opens to form a passage opening. In this state, a fluid can flow through the permanent opening into an interior volume of the duckbill valve 19 and out of the passage opening formed by the duckbill valve slit 22.

The duckbill valve 19 should be configured in such a manner that it cannot roll up and invert such that the duckbill valve slit 22 passes through the permanent opening when, in operation, there is a pressure difference at which a surrounding pressure exceeds a pressure in the interior volume of the duckbill valve 19.

In order to achieve this, two duckbill reinforcements 20 are adhered to an outer side 23 of the duckbill valve wall 21. The duckbill reinforcements 20 are made from polyamide. Owing to their stability, they prevent the duckbill valve wall 21 from rolling up. An inversion of the duckbill valve wall 21 is thereby also effectively prevented.

The duckbill reinforcements 20 are adhered to the duckbill valve wall 21 in such a manner that they respectively extend from one end of the duckbill valve slit 22 in the direction of the valve base 5. A small distance to the valve base 5 is thereby maintained. The duckbill valve reinforcements 20 are thus located in a region of the duckbill valve wall 21 that does not deform to a great extent upon opening and closing of the duckbill valve 19. The region directly at the valve base 5 can act like a flexible joint. The duckbill valve reinforcements therefore only impede opening and closing of the duckbill valve 19 to a limited extent or do not impede this at all.

Figure 2:
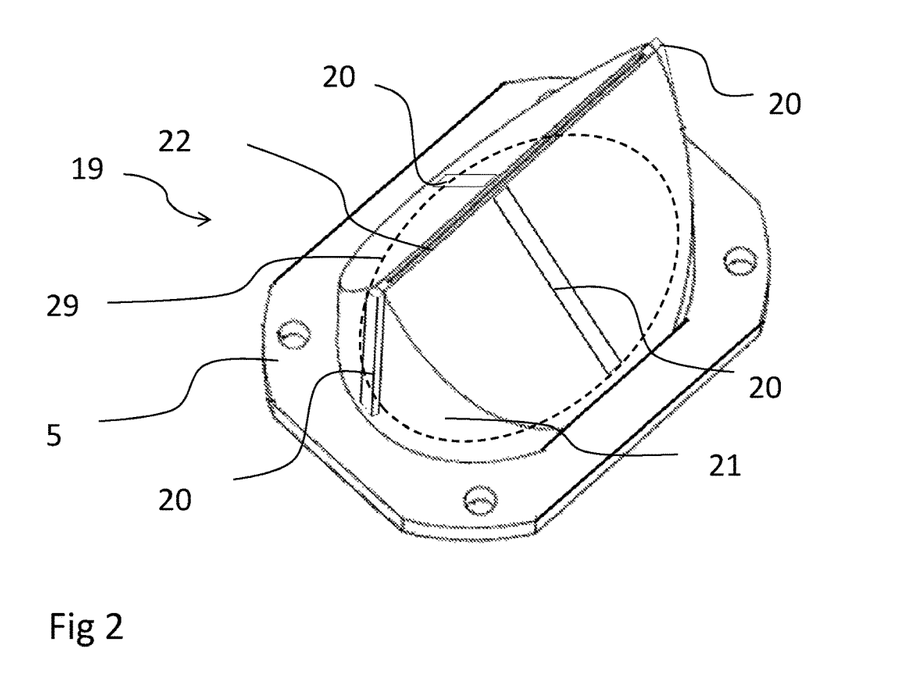
FIG. 2 shows a duckbill valve with four duckbill reinforcements.

FIG. 2 shows a duckbill valve 19 with four duckbill reinforcements 20. The duckbill valve 19 shown in FIG. 2 is similar to the duckbill valve 19 shown in FIG. 1. One difference is that the two duckbill reinforcements 20, which are adjacent to the ends of the duckbill valve slits 22, are not adhered thereto but are rather made from the same material as the duckbill valve wall 21 and the valve base 5 and were produced together with the remaining parts of the duckbill valve 19 as an injection molded part. The material is also a thermoplastic elastomer or a silicone.

Owing to the fact that the wall is thickened by the duckbill reinforcements 20, it receives sufficient stability so that it does not roll up.

Additionally, the duckbill valve 19 also has two further duckbill valve reinforcements 20, which respectively extend from the center of the duckbill valve slit 22 in the direction of the valve base 5. These duckbill valve reinforcements 20 also do not extend right up to the valve base 5 but rather leave a gap so that the movability of the duckbill valve wall 21 is not restricted. These duckbill valve reinforcements 20 are also made of thermoplastic elastomer or silicone and were also produced together with the rest of the duckbill valve 19 as an injection molded part.

Figure 3:
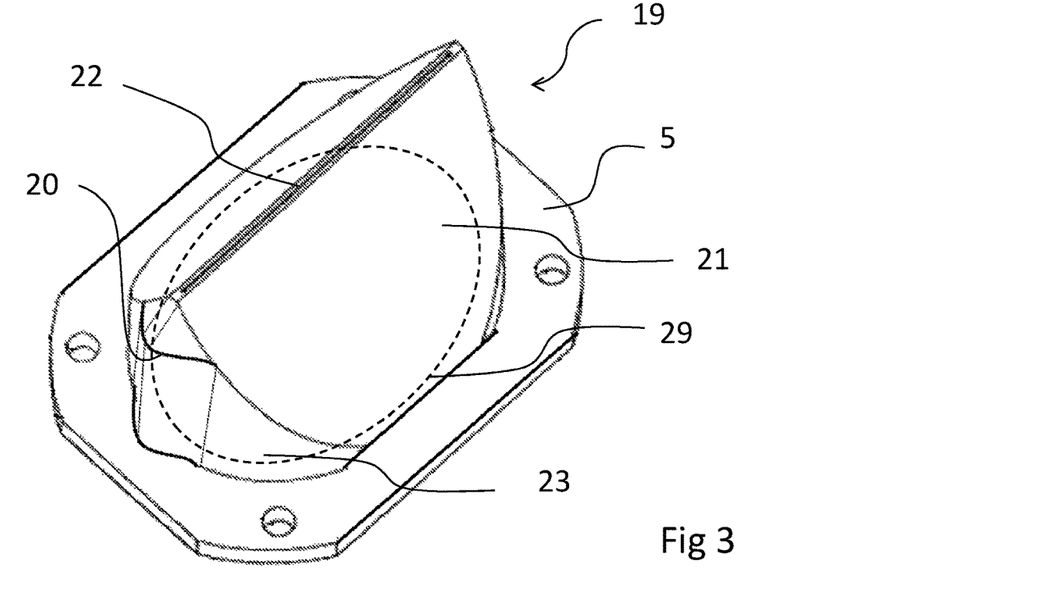
FIG. 3 shows a duckbill valve with one duckbill reinforcement.

FIG. 3 shows a duckbill valve 19 having a duckbill reinforcement 20. The duckbill valve 19 corresponds to the duckbill valves 19 shown in FIGS. 1 and 2, however, the duckbill valve reinforcement 20 is configured in a different manner. Only one duckbill valve reinforcement 20 is provided. It extends on an outer side 23 of the duckbill valve wall 21 from one end of the duckbill valve slit 22 in the direction of the valve base 5. There is also a small gap between the duckbill valve reinforcement 20 and the valve base 5. The duckbill valve reinforcement 20 becomes thinner towards the sides transverse to its direction of extension such that it merges fluently into the duckbill valve wall 21.

Figure 4:
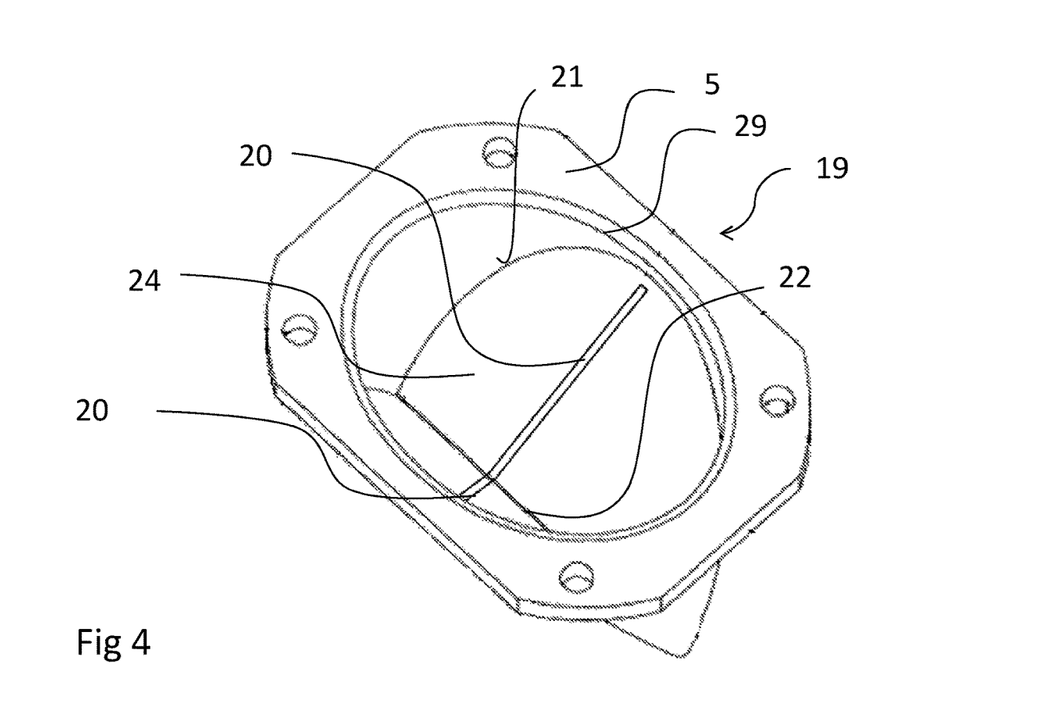
FIG. 4 shows a duckbill valve with two duckbill reinforcements.

FIG. 4 shows a duckbill valve 19 having two duckbill reinforcements 20. The duckbill valve 19 shown in FIG. 4 is similar to the duckbill valve 19 shown in FIG. 2. However, there are only two duckbill valve reinforcements 20. These are provided on an inner side 24 of the duckbill valve wall 21 and extend from the center of the duckbill valve slit 22 in the direction of the valve base 5. There is also a small gap between the duckbill valve reinforcement 20 and the valve base 5.

In the duckbill valve 19 shown in FIG. 4, the duckbill valve reinforcements 20 are also configured to prevent inversion of the duckbill valve 19 without impeding opening and closing of the duckbill valve 19.

Figure 5:
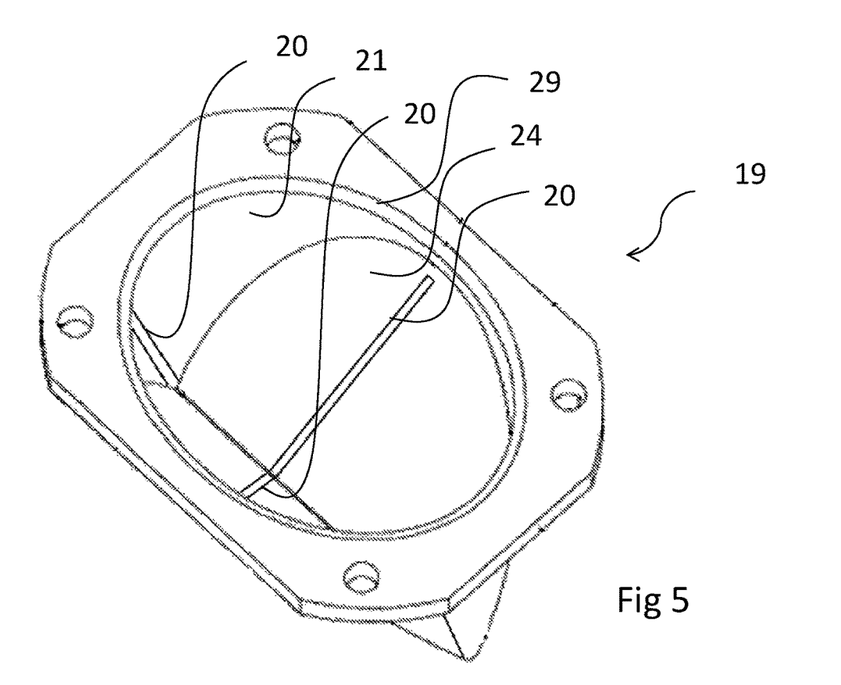
FIG. 5 shows a duckbill valve with four duckbill reinforcements.

FIG. 5 shows a duckbill valve 19 having four duckbill reinforcements 20. Only three of the duckbill reinforcements 5 are visible in FIG. 5. The duckbill valve 19 shown in FIG. 5 is similar to the duckbill valve 19 shown in FIG. 4. However, two additional duckbill valve reinforcements 20 are provided, which extend from the ends of the duckbill valve slit 22 in the direction of the valve base 5. These are also provided on the inner side 24 of the duckbill valve wall 21. A small gap between the duckbill valve reinforcement 20 and the valve base 5 is also provided here.

The opening and closing of the duckbill valve 19 is not impeded by these two additional duckbill valve reinforcements 20 either. Since four duckbill valve reinforcements 20 are provided, the individual duckbill valve reinforcements 20 can be configured so as to be thinner or more flexible than is the case in the duckbill valve shown in FIG. 4 but to nevertheless have the same effect as regards rolling up and inversion.

Figure 6:
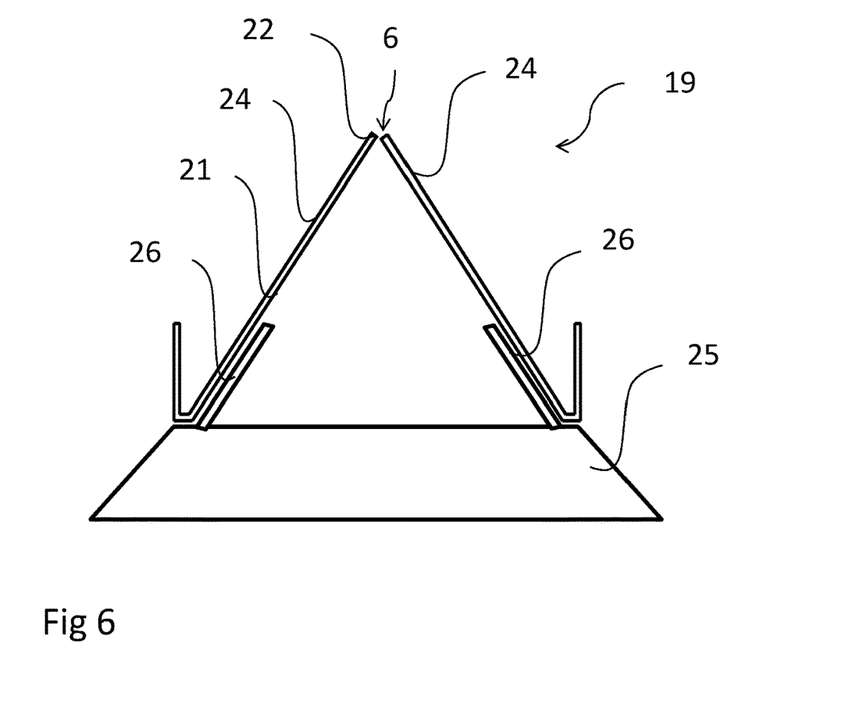
FIG. 6 shows a duckbill valve with two support structures.

FIG. 6 shows a duckbill valve 19 having two support structures 26. The duckbill valve 19 is similar to the duckbill valves 19 shown in FIGS. 1 to 5, however, the duckbill valve wall 21 is not provided with duckbill valve reinforcements 20. The duckbill valve 19 is attached to a valve carrier 25 that is provided with two support structures 26. The two support structures 26 extend along the inner side 24 of the duckbill valve wall 21 in the direction of the duckbill valve slit 22.

Owing to the fact that the support structures 26 are not connected to the duckbill valve wall 21, they do not affect the opening and closing of the valve functional area 6.

The rolling up and inversion of the duckbill valve wall 21 is, however, effectively prevented since the support structures 26 have an abutment edge for a duckbill valve wall 21 and sufficient stability to limit rolling up of the duckbill valve wall 21.

Figure 7:
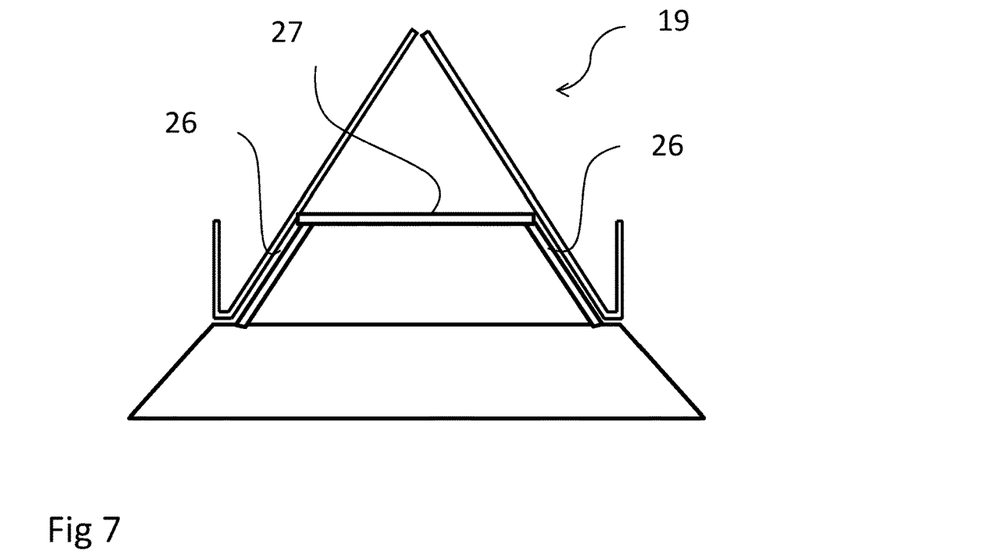
FIG. 7 shows a duckbill valve with two support structures and a passage dividing device.

FIG. 7 shows a duckbill valve 19 having two support structures 26 and a passage dividing device 27. The duckbill valve 19 shown in FIG. 7 is similar to the duckbill valve 19 shown in FIG. 6. The same support structures 26 are provided, however, these are connected with one another by a passage dividing device 27 configured as a bar 27.

The bar 27 causes the passage through the duckbill valve 19 to be divided into two smaller passages. The size of the bodies that can pass through the valve is thereby restricted to a greater extent.

Figure 8:
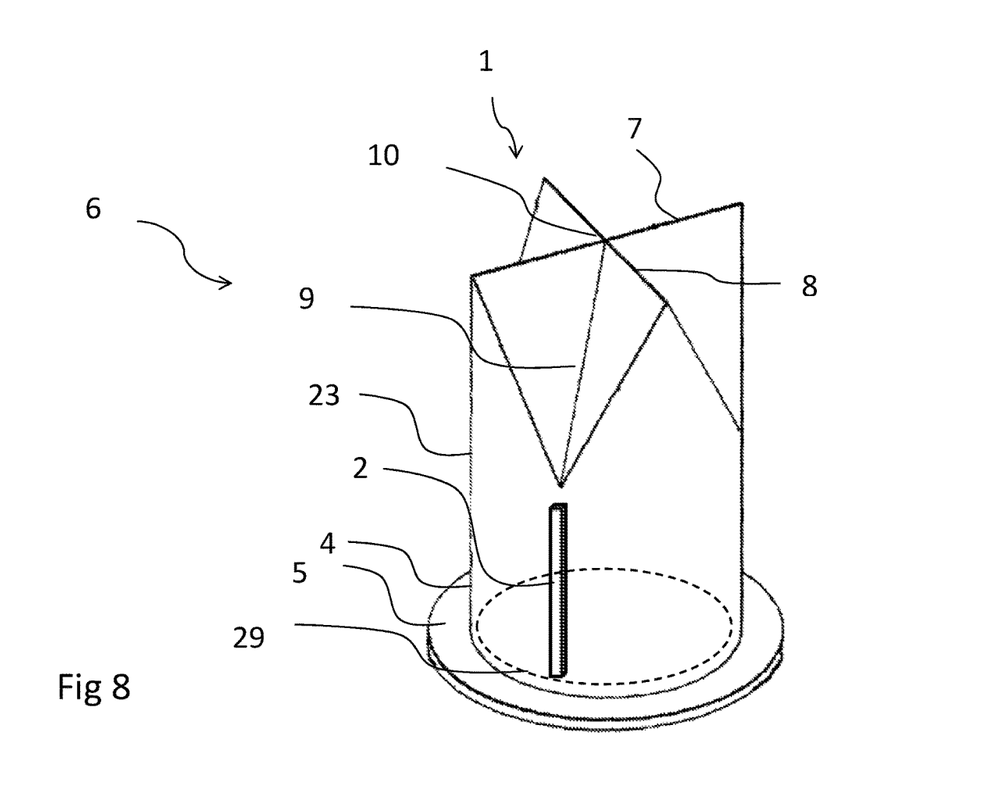
FIG. 8 shows a cross-slit valve with a reinforcing region close to the fold.

FIG. 8 shows a cross-slit valve 1 having a reinforcing region 2 close to the fold. The cross-slit valve 1 comprises a cross-slit valve wall 4 having a cylindrical form, which merges at one end into a valve base 5. A permanent opening 29 is provided in the valve base 5. At the other end of the cylindrical form, the cross-slit valve wall 4 merges into the valve functional area 6 having a first slit 7 and a second slit 8, which are arranged in a cross shape. In the state as shown in FIG. 8, the first slit 7 and the second slit 8 are closed. Four folds 9 are provided, which extend up to the cross-slit valve wall 4 from a central point 10 at which the first slit 7 and the second slit 8 intersect. An internal volume is located inside the cross-slit valve wall 4 between the permanent opening and the valve functional area 6. The reinforcing region 2 that is close to the fold is arranged on an outer side 23 of the cross-slit valve wall 4. The reinforcing region 2 that is close to the fold extends between the endpoint of a fold 9 on the cross-slit valve wall 4 and the valve base 5. The reinforcing region 2 that is close to the fold is thereby at a distance to both the fold 9 and the valve base 5. The material from which the cross-slit valve 1 having the reinforcing region 2 close to the fold is made is silicone. The cross-slit valve 1 having the reinforcing region 2 that is close to the fold has been cast in one piece.

When the pressure in the interior volume exceeds the surrounding pressure and the pressure difference between the interior volume and the surroundings exceeds a predetermined threshold, the first slit 7 and the second slit 8 open to form an opening such that a gas can flow through the permanent opening into the region inside the cross-slit valve wall 4 and out of the opening in the valve functional area 6. The valve functional area 6 thereby deforms. The region of the cross-slit valve wall 4, in which the reinforcing region 2 that is close to the fold is arranged, only deforms to a limited extent or does not deform at all upon opening and closing of the valve functional area 6. The reinforcing region 2 that is close to the fold is at a distance to the fold 9 and the valve base 5 since the cross-slit valve 1 deforms to a greater extent directly at the fold 9 and at the valve base 5 upon opening and closing. The reinforcing region 2 that is close to the fold therefore only impedes opening and closing of the valve functional area 6 to a limited extent or does not do so at all.

When there is a pressure difference at which the surrounding pressure is greater than the pressure in the interior volume, it can occur that the valve functional area 6 is pushed towards the region inside the cross-slit valve wall 4. If a reinforcing region 2 close to the fold were not provided, the valve functional area 6 could pass through the permanent opening such that the cross-slit valve 1 would be inverted. In this process, the cross-slit valve 1 would roll up over the cross-slit valve wall 4. In the embodiment shown in FIG. 8, the reinforcing region 2 close to the fold prevents the rolling up and thus the inversion of the cross-slit valve 1.

Figure 9:
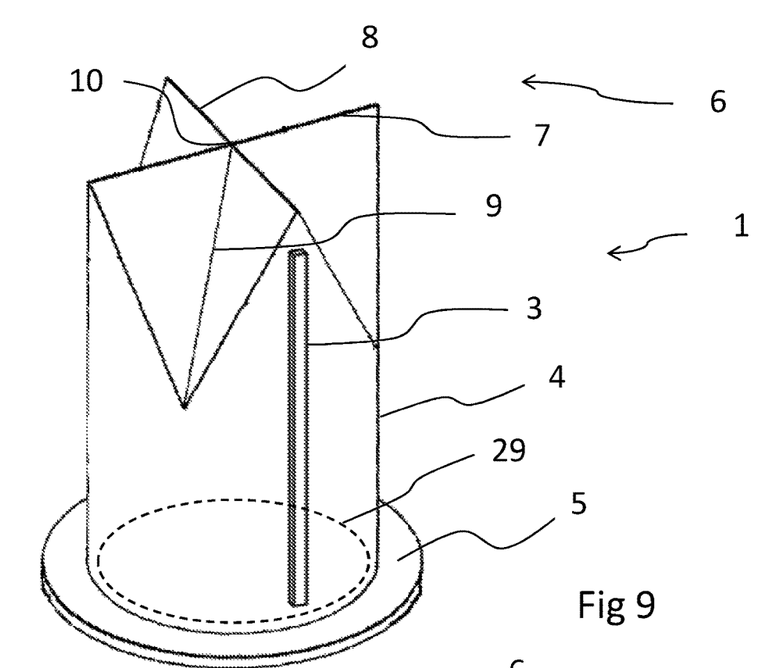
FIG. 9 shows a cross-slit valve with a reinforcing region close to the slit.

FIG. 9 shows a cross-slit valve 1 having a reinforcing region 3 close to the slit. The cross-slit valve 1 shown in FIG. 9 is similar to the cross-slit valve 1 shown in FIG. 8. The difference is that the reinforcing region 3 close to the slit does not abut a fold 9 but rather the second slit 8, whereby a distance to the slit is also maintained. Furthermore, the reinforcing region 3 close to the slit in the cross-slit valve 1 shown in FIG. 9 has not been cast together with the rest of the cross-slit valve 1 but has rather been adhered to the cross-slit valve wall 4. The cross-slit valve 1, with the exception of the reinforcing region 3 that is close to the slit, has been cast from silicone. The reinforcing region 3 that is close to the slit is made from polyamide.

The reinforcing region 3 close to the slit as shown in FIG. 9 is also disposed in a region of the cross-slit valve 1 that only deforms to a limited extent or does not deform at all upon opening and closing. Opening and closing is therefore only impeded to a limited extent or is not impeded at all. Since the reinforcing region 3 that is close to the slit abuts the second slit 8, tearing out of the second slit 8 can be limited on this side.

When there is a pressure difference at which the surrounding pressure is greater than the pressure in the interior volume, the reinforcing region 3 that is close to the slit as is shown in FIG. 9 prevents the rolling up and inversion of the cross-slit valve 1 analogous to the reinforcing region 2 that is close to the fold as shown in FIG. 8. The undesired rolling-up process is stopped slightly earlier than in the cross-slit valve as shown in FIG. 8 since the reinforcing region 3 that is close to the slit is disposed closer to the region of the functional area 5 which comprises an opening depending on the existing pressure difference.

Figure 10:
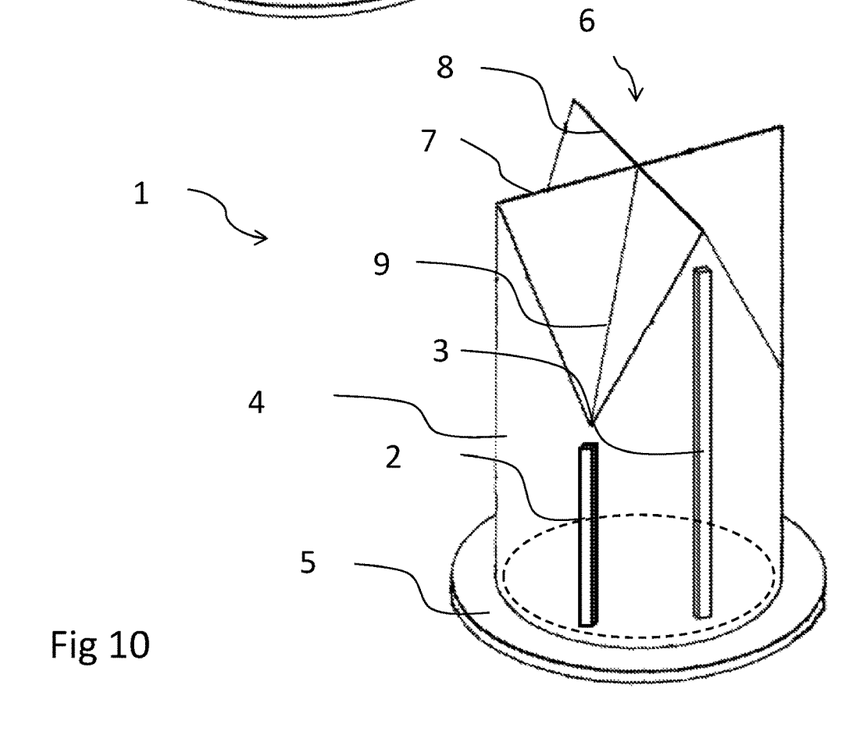
FIG. 10 shows a cross-slit valve with a reinforcing region close to the fold and close to the slit.

FIG. 10 shows a cross-slit valve 1 having a reinforcing region 2 close to the fold and reinforcing region 3 close to the slit. The cross-slit valve 1 corresponds to the cross-slit valves 1 as shown in FIGS. 8 and 9. The reinforcing region 2 close to the fold corresponds to the reinforcing region 2 close to the fold which is shown in FIG. 8, and the reinforcing region 3 close to the slit corresponds to the reinforcing region 3 close to the slit which is shown in FIG. 9.

Owing to the combination of the reinforcing region 2 that is close to the fold and the reinforcing region 3 that is close to the slit, an even better protection against the rolling up and inversion of the cross-slit valve 1 is achieved.

Figure 11:
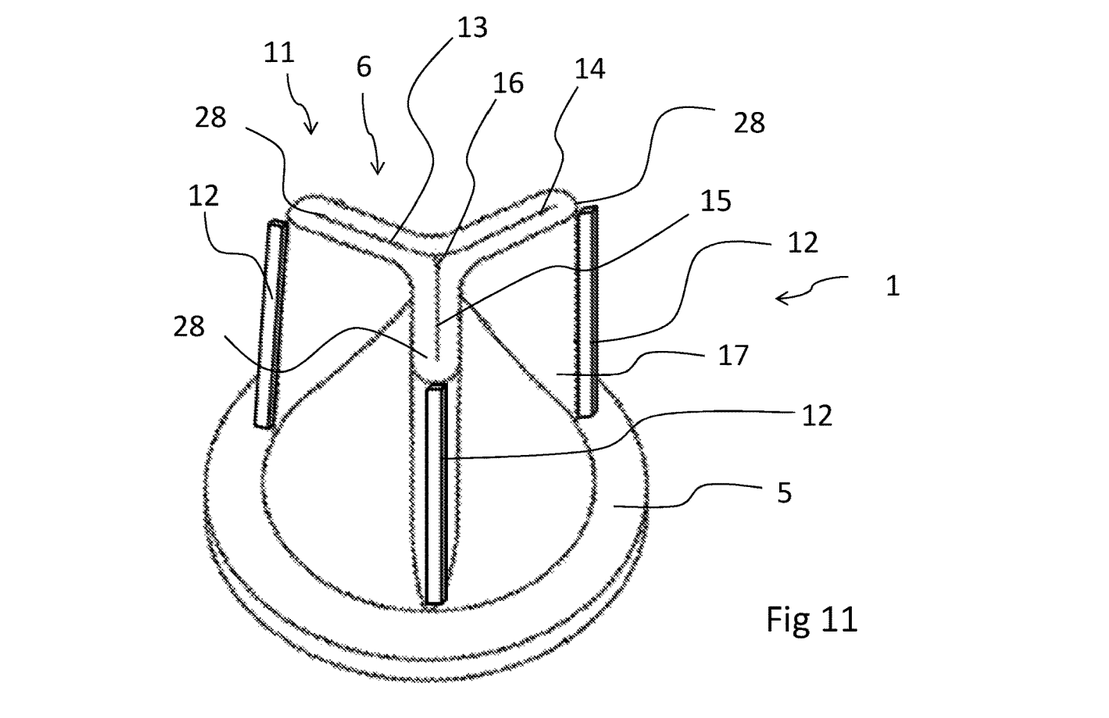
FIG. 11 shows a joker valve with three joker reinforcing regions.

FIG. 11 shows a joker valve 11 having three joker reinforcing regions 12. The joker valve 11 comprises a valve base 5 having a permanent opening that is not shown, a joker valve wall 17 and a valve functional area 6. The joker valve wall 17 surrounds an interior volume that is delimited by the permanent opening and the valve functional area 6. The valve functional area 6 comprises three joker slits 13, 14 and 15, which extend outwardly from a joker central point 16. In the region of the joker slits 13, 14 and 15, the joker valve wall 17 in each case forms a joker fold 28, such that at each joker slit 13, 14 and 15, two joker valve walls 17 lie against one another when the joker slits 13, 14 and 15 are closed.

The three joker reinforcing regions 12 each extend on the joker valve wall 17 from a region that is adjacent to an end of a joker slit 13, 14 and 15 in the direction of the valve base 5. A distance to the valve base 5 is thereby maintained. The joker valve 11, with the exception of the joker reinforcing regions 12, is made from silicone. The joker reinforcing regions 12 comprise polystyrene. The joker valve 11 was produced using the multicomponent injection molding process.

When the pressure in the interior volume increases such that a predetermined pressure difference between the interior volume and the surroundings is exceeded, the joker slits 13, 14 and 15 open to form a passage opening. Since the joker reinforcing regions 12 are located in a region of the joker valve wall 17 that only deforms to a limited extent or does not deform at all upon opening and closing of the joker valve 11, the opening and closing of the joker valve 11 is not affected by the joker reinforcing regions 12.

When the surrounding pressure exceeds the pressure in the interior volume, the valve functional area 6 is pushed in the direction of the permanent opening. The joker reinforcing regions 12 are suitable for preventing the rolling up and inversion of the joker valve 11.

Figure 12:
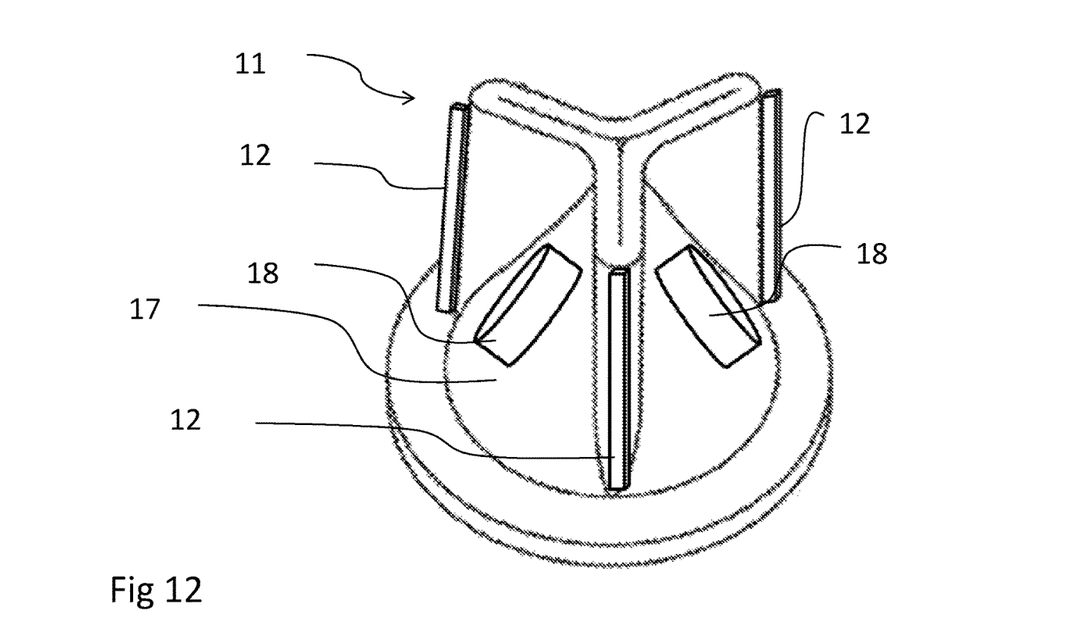
FIG. 12 shows a joker valve with six reinforcing regions.

FIG. 12 shows a joker valve 11 having six reinforcing regions, of which 3 are joker reinforcing regions 12 and 3 are oval reinforcing regions 18. The joker valve 11 shown in FIG. 12 is similar to the joker valve 11 shown in FIG. 11. The difference is that in addition to the 3 joker reinforcing regions 12, 3 oval reinforcing regions 18 are provided. The oval reinforcing regions 12 are provided on the outside of the joker valve wall 17. In a top view, they appear oval. The oval reinforcing regions 18 are made from polystyrene and the joker valve 11 has been produced using the multicomponent injection molding process.

The oval reinforcing regions 18 offer an additional protection against rolling up and inversion.

LIST OF REFERENCE NUMBERS

1 Cross-slit valve
2 Reinforcing region close to the fold
3 Reinforcing region close to the slit
4 Cross-slit valve wall
5 Valve base
6 Valve functional area
7 First slit
8 Second slit
9 Fold
10 Central point
11 Joker valve
12 Joker reinforcing regions
13, 14, 15 Joker slit
16 Joker central point
17 Joker valve wall
18 Oval reinforcing region
19 Duckbill valve
20 Duckbill reinforcement
21 Duckbill valve wall
22 Duckbill valve slit
23 Outer side
24 Inner side
25 Valve carrier
26 Support structure
27 Bar 28 Joker fold
29 Permanent opening

The invention claimed is:

1. A valve for an inhalation device comprising an interior volume that is delimited at least partially by a valve wall, a permanent opening as well as a valve functional area, whereby the valve functional area is configured to be at least almost closed below an opening pressure difference and to be open above the opening pressure difference such that above the opening pressure difference, a fluid can flow through the permanent opening into the interior volume and out of the valve functional area, wherein
the valve comprises an inversion protector that is configured to impede or prevent inversion of the valve wall,
the inversion protector comprises a reinforcing region of the valve wall,
the valve functional area is configured to have a slit below the opening pressure difference,
the reinforcing region is elongated and extends from an end of the slit or from a vicinity of the end of the slit along a shortest path or almost along the shortest path in a direction of the permanent opening, and
the valve wall is invertible, in the absence of the reinforcing region, when a surrounding pressure exceeds a pressure in the interior volume of the valve.

2. The valve according to claim 1, wherein the reinforcing region of the valve wall is at a distance to the permanent opening.

3. The valve according to claim 1, wherein the valve wall comprises a functional material and the reinforcing region of the valve wall comprises a support material which has a higher modulus of elasticity than the functional material.

4. The valve according to claim 1, wherein the reinforcing region of the valve wall abuts the valve functional area.

5. The valve according to claim 1, wherein the inversion protector further comprises a second reinforcing region of the valve wall that abuts the center of the slit below an opening pressure difference.

* * * * *